(12) United States Patent
Naguib

(10) Patent No.: US 6,472,347 B1
(45) Date of Patent: Oct. 29, 2002

(54) CURATIVE SYSTEMIC FUNGICIDAL FORMULATION CONTAINING COPPER ION IN AN EXTREMELY LOW CONCENTRATIONS

(75) Inventor: Amr Ahmed Naguib, Cairo (EG)

(73) Assignee: Delta Agro Chemicals, Cairo (EG)

( * ) Notice: Subject to any disclaimer, the term of this patent is extended or adjusted under 35 U.S.C. 154(b) by 0 days.

(21) Appl. No.: 09/675,120

(22) Filed: Sep. 28, 2000

(30) Foreign Application Priority Data

Nov. 2, 1999 (EG) .............................................. 1380/99

(51) Int. Cl.⁷ ........................ A01N 59/16; A01N 37/00; A01N 25/00; A01N 59/20; A61K 33/34
(52) U.S. Cl. ........................ 504/120; 504/121; 504/313; 424/405; 424/630; 424/637
(58) Field of Search ................................. 424/630, 637, 424/405; 504/120, 121, 313

(56) References Cited

U.S. PATENT DOCUMENTS

| 4,385,134 A | * | 5/1983 | Foscante et al. ............. 523/177 |
| 4,421,569 A | * | 12/1983 | Ditcher et al. ......... 148/6.14 R |
| 4,999,091 A | * | 3/1991 | Doroszkowski et al. ... 204/14.1 |

* cited by examiner

*Primary Examiner*—Alton Pryor
(74) *Attorney, Agent, or Firm*—Thomas R. Vigil; Welsh & Katz, Ltd.

(57) ABSTRACT

The method for forming and the formulation thus formed contains essentially copper salt, acrylic polymer and natural resin in a chelated form and is used as a protective and curative fungicide.

14 Claims, No Drawings

CURATIVE SYSTEMIC FUNGICIDAL FORMULATION CONTAINING COPPER ION IN AN EXTREMELY LOW CONCENTRATIONS

This invention relates to curative fungicidal formulation containing copper ion. The invention concerned with protective/Curative systemic fungicidal formulation containing copper ion in an extremely low concentrations comparing to the currently available preparations.

BACKGROUND OF THE INVENTION

Copper compounds are considered as the earliest compounds used to combat phytopathogenic fungi. The most common copper compounds used as protective fungicides are cuprous oxychlorides, copper oxides and hydroxides. The use of these compounds as fungicides has been restricted to the protective effect. Some copper salts are water-soluble and therefore are used as plant spray whereas salts are deposited on the surface of the plant and kill fungi found on these surfaces. This mode of action is protective mode as it prohibits fungi from penetration into plant tissues. In the meantime, the infected plants remains unaffected with the treatment due to the fact that copper ions are not capable of penetration into plant tissues and therefore, has no curative actions on the fungi found inside the plant tissues. Therefore, use of these salts is restricted to a very narrow scale which is the protective control. Besides, it can not be used in large amounts for environmental safety and human health hazards.

Fungicides are mainly divided into two categories, namely protective fungicides and curative/systemic fungicides. Protective fungicides are fungicides that act to protect plants from fungi by controlling these fungi outside the plants. Curative fungicides are fungicides that penetrate into plant tissues and kill fungi found inside plant tissues. Curative fungicides becomes more valuable if they have a systemic effect i.e. having a capillary movement inside the plant. It is worth noting that curative/systemic fungicides are used in relatively small amounts comparing to protective fungicides.

It is an object of this invention to provide a new curative/systemic fungicidal formulation containing copper salts as an active ingredient. The said formulation is characterized by having a capillary movement inside the plant tissues.

The invention relates also to a method for preparing a new systemic fungicidal formulation to be used curatively whereas copper salts are prepared in a special form that allow copper ions to penetrate into plant tissues and thereby becomes active against fungi. Since this formulation contains copper ions, it has a primary protective effect when sprayed on the plants.

The invention relates also to method of controlling harmful fungi using the new protective/curative formulation. Fungi that can be controlled by this new formulation are the following for example Phytophthora infestans in tomatoes (Late blight)

Pseudoperonospora cubensis in cucumber (Downey mildew)

Plasmopara Viticola in grapes (Downey mildew)

Alternaria solani in tomatoes (Early blight)

Alternaria solani in potatoes (Early blight)

Mycospharilla fragari in strawberry (Leaf Spot)

Alternaria puri in onion (Purple blotch)

Brimia lactota in lettuce (Downey mildew)

Cercosporidium personatum in peanut (Leaf spot)

Alternaria alternata in sunflower (Leaf spot)

Botrytus faba in bean (Leaf spot).

These and other advantages will become apparent after reviewing the detailed description.

DETAILED DESCRIPTION

It is well known that copper salts have a fungicidal activity and some are soluble in water, however, normal solutions of these salts do not permit copper ions to penetrate into plant tissues. We have discovered that dissolving copper salts in water-soluble polymeric media allow copper ions to penetrate into plant tissues thereby controlling fungi found inside plant tissues.

The formulation of this invention is stable for quite a long time with no alteration of chemical or physical properties. Moreover, the said formulation can be diluted with water and form a solution.

The formulation of this invention consists mainly of copper salt in a chelated form with polymeric media and natural resin. Copper salt used in the present formulations is Copper sulfate. The normal form of this salt is soluble, non-odor crystals or granules, chemical structure is $CuSO_4$, molecular weight 159.60.

Polymeric material used in the formulation of this invention is an acrylic polymer with a molecular weight in the range of from 1.5–2.5 million and preferably in the range of 1.9–2.1 million.

The natural resin used in the formulation of this invention is a resin having a molecular weight in the range of 200–400 and preferably 250–320.

Polymeric material plays an important role in the subject formulation and enhances the adhesion power on the treated surfaces so that it can not be washed out from the plant surface by rainfall or due to wind. Moreover, the said polymeric material forms a thin film that covers copper ions which makes the copper ion capable of penetrating plant tissues in a controlled extended manner. In other words, the polymeric material sticks primarily to the surface of the plant and allows the copper ions to penetrate into plant tissues for extended period which acquires the formulation a retarded fungicidal activity extended for a longer period.

The formulation of the invention can be prepared by dissolving the three components separately in water. Copper salt is dissolved in water with agitation. Polymeric material is completely dissolved in water until forming a solution. Natural resin is dissolved in water until obtaining a homogeneous solution.

Copper solution is added to acrylic polymer with continuous agitation Until obtaining a homogeneous mixture. Then resin solution is added with continuous agitation until complete mixing and obtaining a homogeneous solution.

The resulting formulation is an opaque greenish solution with a viscosity of 70–75 cps as measured by Brookfield LV viscometer of 12 rpm. The pH of the said solution is 3.2. The formulation is stable at 5–50 C. without changes in the chemical or physical properties. This formulation can be stored for quite long period of time at the normal room temperature.

Concentration of copper ion in the formulation is 4–7% and preferably 5–6% whereas concentration of acrylic polymer is 1–12% and preferably 2–10% and natural resin 2–30% and preferably 5–25%.

The following examples illustrate the invention in details and should not be construed as being limitation on the scope and spirit thereof.

EXAMPLE (1)

Penetration of the New Formulation Inside Plant Tissues

Non Organic copper compounds have been used as protective fungicides for quite a long time, but could not be used as curative fungicides due to the fact that copper ions are not capable of penetrating into plant tissues. We have tested penetration of copper ions found in the new formulation applying one of two methods:

First method: inspection of plant tissue to follow copper ions pathway in cucumber leaves.

Second method: by determining of copper concentration in cucumber leaves before and after washing.

Procedures

In this test, two week cucumber plants grown in pots at the greenhouse of the Central Agricultural Pesticides Lab were used.

Three concentrations of the new formulation of the invention were prepared by diluting with distilled water (1%, 5% and 10%). Cucumber plants were sprayed and left to dry for approximately one hour.

Treated leaves from each concentration were divided into two groups. The first group was thoroughly washed with water using sprayer for about 10 minutes to ensure removal of all residues from the surface, while the second group was left without washing.

Transverse sections of treated leaves were taken using rotary microtome at a thickness of 3–5 microns.

Transverse sections were mounted on glass slides and stained using Rubeanic acid method (Howqell 1959 ) which indicates copper ions as greenish black granules. Stained leaf sections were microscopically examined and photographed using Olympus microscope mounted with 35 mm camera.

This is clearly indicates that use of acrylic polymer according to this invention leads to penetration of copper ions into plant tissues.

EXAMPLE (2)

Efficacy Against Alternaria-Solani in Tomato

This test was made on field planted with Tomato plants var. Joker. Chemicals used in this test are shown in the following table.

| Formulations | Active ingredient | Form | Dosage per (100 ft.water) |
|---|---|---|---|
| Present formulation | Metallic copper 6% | Liquid | 150 cc. |
| Present formulation | Metallic copper 6% | Liquid | 200 cc. |
| Present formulation | Metallic copper 6% | Liquid | 250 cc. |
| Present formulation | Metallic copper 6% | Liquid | 300 cc. |
| Cupravit 0b21 (Standard) | Metallic copper 50% | WP | 500 gr. |

The test initiated on Jun. 19, 1999 when disease conditions and early symptoms of disease became apparent in accordance with random plots test pattern. The trial was conducted on plots each of 40 m² of land and each having at least 60 plants. Four replicates were made for each test.

Spraying began when disease was first observed on 19.06.1999 and it was applied two times at 10 days intervals.

Plants were observed and evaluated using the following 0 to 5 scale:

| | |
|---|---|
| 0 | No disease |
| 1 | A few spots on lower leaves of the plant |
| 2 | 25% of the plant is infected |
| 3 | 50% of the plant is infected |
| 4 | 75% of the plant is infected |
| 5 | plant is totally infected and died.. |

Disease index as well as efficacy of the formulation was calculated using Abbott formula.

Results are shown in the following table (1).

TABLE 1

| Formulation | Repeat | Disease index | Disease Severity | Efficacy % |
|---|---|---|---|---|
| Formulation | I | 0.45 | 9.00 | 60.1% |
| Of the invention | II | 0.57 | 11.4 | 66.4% |
| 150 cc | III | 0.72 | 14.4 | 61.2% |
| | IV | 0.43 | 6.6 | 65.3% |
| | Average | 0.54 | 10.85 | 63.25 |
| Formulation | I | 0.38 | 7.6 | 66.3% |
| Of the invention | II | 0.51 | 10.2 | 70.0% |
| 200 cc | III | 0.53 | 10.6 | 71.5% |
| | IV | 0.43 | 8.6 | 65.3% |
| | Average | 0.46 | 925 | 68.27% |
| Formulation | I | 0.28 | 5.6 | 75.0% |
| Of the invention | II | 0.48 | 9.6 | 71.7% |
| 250 cc | III | 0.43 | 8.6 | 76.8% |
| | IV | 0.33 | 6.6 | 73.3% |
| | Average | 0.38 | 7.6 | 74.25% |
| Formulation | I | 0.12 | 2.4 | 89.3% |
| Of the invention | II | 0.31 | 6.2 | 81.7% |
| 300 cc | III | 0.30 | 6.0 | 83.8% |
| | IV | 0.16 | 3.2 | 87.0% |
| | Average | 0.25 | 4.45 | 85.45% |
| Cupravit 0b21 | I | 0.24 | 4.8 | 77.9% |
| Standard | II | 0.28 | 5.6 | 83.1% |
| | III | 0.38 | 7.6 | 79.5% |
| | IV | 0.18 | 3.6 | 85.4% |
| | Average | 0.27 | 5.4 | 81.47% |
| Untreated | I | 1.13 | 22.6 | |
| Control | II | 1.7 | 34.0 | |
| | III | 1.86 | 37.3 | |
| | IV | 1.24 | 24.8 | |
| | Average | 1.48 | 29.67 | |

As shown in the above table, it appeared that the formulation of the invention is very effective, comparing with the standard, when used at a concentration equal to 300 cc and has no Phytotoxic effect on Tomato Plants. It is also noted that disease severity of plants treated with the formulation of the invention has been greatly reduced in comparison with the control plants, which further confirm the activity of the formulation of the present invention. Curative effect is also indicated by the high efficacy index against Alternaria-solani.

EXAMPLE 3

Efficacy Against Pseudoperonospora Cubensis in Cucumber

In this test, experimental area was divided into identical units each of 45.4 m2. The said units are planted with Beit Alpha cucumber seeds which is considered one of the most susceptible varieties against the Downy mildew. Seeds are cultivated on Apr. 15, 1998 and all agricultural practices (irrigation, fertilization, pest control were made according to standard techniques.

The formulation of the invention were used at rates of 1:100, 1:200, 1:300 and 1:400 and for comparison purposes Copper OxyChloride (PERECOPPER) was used at 25 g/10 L water and PREIVCUR N which was used at 25 cc/10 L water. Untreated area was used as a check. Each experiment is replicated four times.

The plots were first sprayed on May 27, 1998 when first symptoms of infestation appeared using Knapsack sprayer of 10 L capacity. Second spray was made on Jun. 8, 1998 using knapsack sprayer of 18 L.

Third spray was made on Jun. 18, 1998 using the latter sprayer used in the second spray. Both sides of plant leaves were covered thoroughly with the formulations. Untreated plots were left without spraying at the first treatment and sprayed with equal volume of water at the second and third treatments. Severity of infestation was determined and evaluated using Horsfall Barratt scale of 0 to 11.

| Degree of infection | Range of infection | % |
|---|---|---|
| 0 | 0 | 1.17 |
| 1 | 0–3 | 2.34 |
| 2 | 6–3 | 4.68 |
| 3 | 12–6 | 9.37 |
| 4 | 12–25 | 18.75 |
| 5 | 25–50 | 37.5 |
| 6 | 50–75 | 62.5 |
| 7 | 75–88 | 81.25 |
| 8 | 88–94 | 90.63 |
| 9 | 94–97 | 95.31 |
| 10 | 97–100 | 97.66 |
| 11 | 100 | 98.82 |

It should be noted that the spraying volume was 10 liters in the first treatment and 15–18 Liters in the second and third treatments. Results obtained are shown in the following table.(2)

TABLE (2)

| Formulation | Rate | Severity of infection After 1st treatment | 2nd treatment | 3rd treatment |
|---|---|---|---|---|
| Invention | 1:100 | 5.1 | 2.9 | 16.9 |
| Invention | 1:200 | 9.4 | 5.8 | 39.9 |
| Invention | 1:300 | 8.0 | 8.7 | 39.7 |
| Invention | 1:400 | 9.4 | 9.0 | 51.3 |
| Copper Oxy Chloride | 250 gm/100 Liters | 8.9 | 9.1 | 28.4 |
| PREIVCUR N | 250 cc/100 L | 4.4 | 7.8 | 30.1 |
| Untreated control | — | 12.7 | 30.9 | 44.0 |

As shown in the above table, the formulation of the invention was very active at a rate of 1:100 against downy mildew and the formulation of the invention at rates of 1:100 or 1:200 can give excellent results against this disease.

EXAMPLE 4

Efficacy against Plasmopara Viticola in Grapes

In this test red grapes has been used. The formulation of the invention was used at rates 1:100, 1:200, 1:300 and 1:400. Galben Copper was used as standard control. Four replicates were made Plants sprayed on 4.6.1998 and repeated 5 times at intervals of 15 days. Results are shown in the following table (3).

TABLE (3)

| Compound | Concentration | Severity of infection | Efficacy % |
|---|---|---|---|
| Invention | 1:100 | 23.75 | 55.68% |
| Invention | 1:200 | 13.83 | 79.3% |
| Invention | 1:300 | 11.83 | 75.80% |
| Invention | 1:400 | 25.33 | 58,4% |
| Galben Copper | 2.5 gm/L | 19.41 | 66.04 |
| Control | — | 57.16 | 00.00 |

The above results indicate that the formulation of the invention is active against Plasmopara Viticola and performed an efficacy of 79% when used at a rate of 1:200 this efficacy exceeded the efficacy of the standard fungicide (66%) used for comparison.

EXAMPLE (5)

Efficacy Against Alternaria-solani in Potato

Potato plants Diamont variety were used in this test. Plants were cultivated on Jan. 28, 1998 and treated 6 weeks after plantation. Three replicates were used for each treatment. The invented formulation was used at rates shown in table 4. For comparison, Ridomil plus was used at rate of 150 gm/100 L water.

First spray was carried out after 6 weeks from cultivation. Treatment is repeated twice at 15 days intervals. Spraying was carried out before the symptoms of the disease become apparent. Results are shown in table (4).

TABLE (4)

| Compounds | Conc. | Severity of infection after spraying | | | Total | Average |
|---|---|---|---|---|---|---|
| | | 1st | 2nd | 3rd | | |
| Invention | 1:100 | 4.79 | 4.41 | 2.86 | 12.06 | 4.02 |
| Invention | 1:200 | 10.71 | 3.26 | 14.13 | 28.1 | 9.36 |
| Invention | 1:300 | 10.5 | 9.52 | 7.69 | 28.71 | 9.24 |
| Invention | 1:400 | 10.14 | 11.36 | 12.33 | 33.83 | 11.28 |
| Ridomil plus | 150 gm/100 L | 8.33 | 10.58 | 14.06 | 32.97 | 10.99 |
| Control | — | 32.14 | 41.67 | 38.33 | 112.14 | 37.38 |

As shown in table 4, the invented formulation was very active against early blight in Potato particularly when used at a rate of 1:100.

EXAMPLE (6)

Efficacy Against Pseudoperonospora Cubensis In Cucumber

This trial was conducted in a field planted with Octopus—SG 7023 pickle-cucumber. Compounds used in this test are shown in the following table.

| Compounds | Concentrations of Active ingredient | Form | Rate per 100 L water |
|---|---|---|---|
| Invention | Metallic copper 6% | Liquid | 150 cc |
| Invention | Metallic copper 6% | Liquid | 200 cc |
| Invention | Metallic copper 6% | Liquid | 250 cc |
| Invention | Metallic copper 6% | Liquid | 300 cc |
| Tri-Miltox Forte | Mancozeb (20% W/W) Metallic copper (21% W/W) | WP | 250 g |

-continued

| Compounds | Concentrations of Active ingredient | Form | Rate per 100 L water |
|---|---|---|---|
| Ridomil MZ 72 | Mancozeb (64%) Metallic copper (8%) | WP | 250 g |

The test was initiated on Jun. 6, 1999 when disease conditions and early symptoms of the disease became apparent. Tests were carried out with four replicates. Spraying was carried out by low pressurized conventional knapsack sprayer.

Spraying began when disease was first observed (20.06.1999) and it was applied two times at 10 days intervals. Spraying volume started with 13 Liters in the first treatment and 20 Liters in the second and third treatments. Evaluation and determination of chemical efficacy was made by counting on 100 leaves taken from each test after ten days from the last treatment. Evaluation was made in accordance with the following scale:

| Scale | Severity of infection |
|---|---|
| 0 | No spots on leaves |
| 1 | 1–5% of leaves infected |
| 2 | 6–10% of leaves infected |
| 3 | 11–25% of leaves infected |
| 4 | 26–50% of leaves infected |
| 5 | More than 50% of leaves infected |

Disease index as well as efficacy of the formulation was calculated using Abbott formula.

Results are shown in the following table (5).

TABLE (5)

| Compounds | Replicates | Disease index | Disease Severity | Efficacy % |
|---|---|---|---|---|
| Composition | I | 0.63 | 12.6 | 62.0% |
| of the invention | II | 0.43 | 8.6 | 68.3% |
| 150 cc | III | 0.37 | 7.4 | 66.9% |
|  | IV | 0.44 | 8.8 | 63.6% |
|  | Average | 0.46 | 9.35 | 65.2% |
| Formulation | I | 0.41 | 8.2 | 75.3% |
| Of the Invention | II | 0.36 | 7.2 | 73.5% |
| 200 cc | III | 0.34 | 6.8 | 69.6% |
|  | IV | 0.28 | 5.6 | 76.8% |
|  | Average | 0.34 | 6.95 | 73.8% |
| Formulation | I | 0.33 | 6.6 | 80.1% |
| Of the Invention | II | 0.16 | 3.2 | 88.2% |
| 250 cc | III | 0.25 | 3.0 | 86.6% |
|  | IV | 0.22 | 4.4 | 81.8% |
|  | Average | 0.24 | 4.3 | 74.17% |
| Formulation | I | 0.30 | 6.0 | 81.9% |
| Of the Invention | II | 0.13 | 2.6 | 90.4% |
| 300 cc | III | 0.18 | 3.6 | 83.9% |
|  | IV | 0.15 | 3.0 | 87.6% |
|  | Average | 0.19 | 3.8 | 85.95% |
| Tri-Miltox | I | 0.28 | 5.6 | 77.9% |
| Forte | II | 0.30 | 6.0 | 84.8% |
|  | III | 0.17 | 3.4 | 76.0% |
|  | IV | 0.29 | 5.8 | 76.0% |
|  | Average | 0.26 | 5.2 | 80.45% |
| Ridomil MZ 72 | I | 0.23 | 4.6 | 86.1% |
|  | II | 0.26 | 5.2 | 80.8% |
|  | III | 0.21 | 4.2 | 81.2% |
|  | IV | 0.18 | 3.6 | 85.1% |
|  | Average | 0.22 | 4.4 | 83.3% |

TABLE (5)-continued

| Compounds | Replicates | Disease index | Disease Severity | Efficacy % |
|---|---|---|---|---|
| Control | I | 1.66 | 33.2 |  |
|  | II | 1.36 | 27.2 |  |
|  | III | 1.12 | 22.4 |  |
|  | IV | 1.21 | 24.2 |  |
|  | Average | 1.33 | 26.75 |  |

This results clearly show the effectiveness of the formulation of the present invention as curative fungicide in addition to the protective basic activity. Control group shows that infection severity in the test area was about 26.75% but the efficacy of the formulation of the present invention when used at rates of 150, 200, 250 and 300 cc were equal to 65.2%, 73.8%, 84.17% and 85.95% respectively. In other words severity of infection has been reduced to only 3–4% and these result demonstrate the activity and superiority of the present formulation when used at a rate of 300 cc whereas it shows an efficacy of 85.95% whereas the efficacy of Tri-Miltox Forte was 80.45% and Ridomil MZ 72 was 83.3%.

On the other hand, spraying the formulation of the invention or leaves lead to reduction of disease index (protective effect) from 1.33 to 0.19 when used at a rate of 300 cc.

EXAMPLE (7)

Efficacy against Phytophthora Infestans in Tomato

This trial was conducted in a field planted with Tomatoes variety Alta. Formulations used in this test are shown in the following table.

| Formulation | Active ingredient Concentration | Form | Rate per 100 L water |
|---|---|---|---|
| Invention | Metallic copper 6% | Liquid | 150 cc |
| Invention | Metallic copper 6% | Liquid | 200 cc |
| Invention | Metallic copper 6% | Liquid | 250 cc |
| Invention | Metallic copper 6% | Liquid | 300 cc |
| Cupravit 0b21 | Metallic copper 50% | WP | 500 g |
| Sandofan M | Oxadixyl (10% W/W) + Mancozeb (56% W/W) | Liquid | 200 cc |

The test was initiated on Jun. 21, 1999 when disease conditions and early symptoms of the disease became apparent. Tests were carried out with four replicates. Spraying was carried out by low pressurized conventional knapsack spryer.

Spraying began when disease was first observed and it was applied two times at 10 days intervals. Spraying volume started with 14 Liters in the first treatment and 16 Liters in the second and third treatments. Evaluation was made in accordance with the following scale:

| Scale | Severity of infection |
|---|---|
| 0 | No infection |
| 1 | 1 out of 10 leaves infected |
| 2 | All leaves are infected but plant still green |
| 3 | 50% of leaf surfaces infected with necrosis |
| 4 | 75% of leaf surface infected with necrosis |
| 5 | All leaf surface infected and plant died |

Disease index as well as efficacy of the formulation was calculated using Abbott formula.

Results are shown in the following table (6.)

TABLE 6

| Formulation | Repeat | Disease index | Disease Severity | Efficacy % |
|---|---|---|---|---|
| Formulation | I | 0.44 | 8.8 | 63.6 |
| Of the invention | II | 0.40 | 8.0 | 70.3 |
| 150 cc | III | 0.49 | 9.8 | 65.9 |
|  | IV | 0.26 | 5.2 | 67.9 |
|  | Average | 0.39 | 7.95 | 66.92 |
| Formulation | I | 0.39 | 7.8 | 67.7 |
| Of the invention | II | 0.34 | 6.8 | 74.8 |
| 200 cc | III | 0.43 | 8.6 | 70.1 |
|  | IV | 0.22 | 4.4 | 72.8 |
|  | Average | 0.34 | 6.9 | 71.35 |
| Formulation | I | 0.27 | 5.4 | 77.6 |
| Of the invention | II | 0.21 | 4.2 | B4.4 |
| 250 cc | III | 0.25 | 3.0 | 82.6 |
|  | IV | 0.17 | 3.4 | 79.0 |
|  | Average | 0.22 | 4.5 | 80.9 |
| Formulation | I | 0.22 | 4.4 | 81.8 |
| Of the invention | II | 0.18 | 3.6 | 86.6 |
| 300 cc | III | 0.29 | 5.8 | 79.8 |
|  | IV | 0.09 | 1.8 | 88.8 |
|  | Average | 0.19 | 3.9 | 84.25 |
| CupralVt 0b21 | I | 0.28 | 5.6 | 76.8 |
|  | II | 0.24 | 4.8 | 82.2 |
|  | III | 0.35 | 7.0 | 75.6 |
|  | IV | 0.16 | 3.2 | 80.2 |
|  | Average | 0.25 | 5.15 | 78.7 |
| Sandofan M | I | 0.16 | 3.2 | 86.7 |
|  | II | 0.31 | 6.2 | 77.0 |
|  | III | 0.29 | 5.8 | 79.8 |
|  | IV | 0.12 | 2.4 | 85.1 |
|  | Average | 0.22 | 4.4 | 82.15 |
| Control | I | 1.21 | 24.2 |  |
|  | II | 1.35 | 28.0 |  |
|  | III | 1.44 | 28.8 |  |
|  | IV | 0.81 | 16.2 |  |
|  | Average | 1.20 | 24.05 |  |

These results clearly show the effectiveness of the formulation of the present invention. Control group shows that infection severity in the test area was about 24%. The efficacy of the formulation of the present invention when used at rates of 150, 200, 250 and 300 cc were 65.2%, 73.8%, 84.17% and 85.95% respectively. In other words severity of infection has been reduced from 24% to only 3.9% when formulation of the invention is used at a rate of 300 cc while it has been reduced to 5.15% and 4.4% in case of using Cupravit and Sandofan, respectively.

EXAMPLE (8)

Determination of Copper Residues in the Form of Metallic Copper or as Copper Sulfate in Grape Leaves and Fruits Copper residues either as copper or as a copper sulfate were determined using atomic absorption spectrophotometric methods. Test was conducted in Ganaklis grape farms. A grape trees var. Romi was sprayed on Jul. 20, 1999 at a rate of 60.00 g a.i. per feddan. Different plot was selected in the same farm to serve as a control. Eight samples (fruits or leaves) from the treated and untreated trees were collected at random after one hour of spray then after 7, 14, 21, 23 and 25 days after treatment and then at harvesting (26 days).

Each sample was placed in plastic bag and stored in deep freezer at −20 C. until ready for analysis. Samples of grapes (fruits and leaves ) were digested in a muffle furnace at 500 C. for 3 hours (Dry aching technique) and analysed using Atomic absorption spectrophotometer.

Each sample was dried in an oven at 65 C. overnight, ground it and stored in tightly thoroughly closed bottles. One g of each sample (in duplicate ) was placed in porcelain crucible. Crucibles were pre ached on a flame for 5 minutes and transferred to muffle furnace at 500 C. to allow to ash for 2 hours. After removing crucibles from muffle, it was cooled. Ash was wetted by adding 10 drops of a solution containing $H_2O + HNO_3$ (1:1)

The crucibles were heated on a hot plate set at 100–120 C. to evaporate excess $HNO_3$. The crucibles were returned to muffle and ached for one hour at 500 C. after cooling the crucibles; the ash was dissolved in 10 ml H CL (1+1) and transferred quantitatively to 50 ml volumetric flask. Result of grape fruits analysis are shown in table (7 ) whereas results of grape leaves are shown in table (8 ) ( p. p.m. indicate parts per million).

TABLE 7

| Time of treatment | Untreated PPM | Treated PPM | Difference PPM | Residues as copper sulfate |
|---|---|---|---|---|
| 1 Hour | 0.298 | 2.202 | 1.904 | 7.464 |
| 7 days | 0.349 | 1.664 | 1.315 | 5.155 |
| 14 days | 0.352 | 1.662 | 1.310 | 5.135 |
| 21 days | 0.389 | 1.292 | 0.903 | 3.539 |
| 23 days | 0.407 | 1.122 | 0.715 | 2.803 |
| 25 days | 0.329 | 0.832 | 0.503 | 1.972 |
| 26 days | 0.308 | 9.548 | 0.240 | 0.941 |

TABLE 8

| Time of treatment | Untreated PPM | Treated PPM | Difference PPM | Residues as copper sulfate |
|---|---|---|---|---|
| 1 hour | 5.317 | 10.760 | 5.443 | 21.336 |
| 7 days | 4.397 | 7.935 | 3.538 | 13.869 |
| 14 days | 4.152 | 6.875 | 2.723 | 10.674 |
| 21 days | 4.047 | 6.765 | 2.718 | 10.654 |
| 23 days | 4.202 | 5.820 | 1.618 | 6.342 |
| 25 days | 2.024 | 3.340 | 1.316 | 5.158 |
| 26 days | 2.065 | 3.091 | 1.026 | 4.022 |

As already known, permissible concentrations for copper residues are 20 ppm for vegetables and fruits. This indicates that the residues do not exceed the permissible limits after 7 days from treatment and accordingly the formulation of the invention is quite safe for consumers.

Although the formulation of the invention is a liquid, it is possible to formulate other forms e.g. emulsions, suspensions, powders, wettable powders and others without departing from the scope of this invention.

What is claimed is:

1. A fungicidal composition for treating phytopathogenic fungi comprising:

Phytophthora infestans in tomatoes and potatoes (Late blight)

Pseudoperonospora cubensis in cucumber (Downey mildew)

Plasmopara Vicicola in grapes (Downey mildew)

Alternaria solani in tomatoes (Early blight)

Alternaria solani in potatoes (Early blight)

Mycospharilla fragari in strawberry (Leaf Spot)

Alternaria puri in onion (Purple blotch)

Brimia lactota in lettuce (Downey mildew)

Cercosporidium personatum in peanut (Leaf spot)

Alternaria alternata in sunflower (Leaf spot)

Botrytus faba in bean (Leaf spot)

said composition consisting essentially of:
- 4–7% by weight copper salt;
- 1–12% by weight acrylic polymer;
- 2–30% by weight natural resin; and
- 51–93% by weight water.

2. The fungicidal composition according to claim 1 wherein the copper salt is copper sulfate.

3. The fungicidal composition of claim 1 wherein the acrylic polymer has a molecular weight of from 1.5–2.5 million.

4. The fungicidal composition of claim 3 wherein the acrylic polymer has a molecular weight between 2 and 2.3 million.

5. The fungicidal composition of claim 1 wherein the natural resin has a molecular weight of between 200 and 400.

6. The fungicidal composition of claim 5 wherein the natural resin has molecular weight of between 250 and 320.

7. The fungicidal composition of claim 1 wherein said copper salt is between 5 and 6% by weight.

8. The fungicidal composition of claim 1 wherein said acrylic polymer is between 2 to 10% by weight.

9. The fungicidal composition of claim 1 wherein said natural resin is between 5 and 25% by weight.

10. The fungicidal composition of claim 1 being formed by chelating copper salt with acrylic polymer and natural resin by dissolving copper salt in water with agitation, by dissolving acrylic polymer in water with agitation and by dissolving natural resin in water with agitation.

11. The fungicidal composition of claim 10 wherein the resulting agitated composition has an opaque greenish color, a viscosity similar to glycerin viscosity and a pH of approximately 3.2.

12. The fungicidal composition of claim 10 having a viscosity of between 57 and 62 cps.

13. A method for treating phytopathogenic fungi comprising:
- Phytophthora infestans in tomatoes (Late blight)
- Pseudoperonospora cubensis in cucumber (Downey mildew)
- Plasmopara Vicicola in grapes (Downey mildew)
- Alternaria solani in tomatoes (Early blight)
- Alternaria solani in potatoes (Early blight)
- Mycospharilla fragari in strawberry (Leaf Spot)
- Alternaria puri in onion (Purple blotch)
- Brimia lactota in lettuce (Downey mildew)
- Cercosporidium personatum in peanut (Leaf spot)
- Alternaria alternata in sunflower (Leaf spot)
- Botrytus faba in bean (Leaf spot)

comprising the steps of:
- chelating copper salt with; acrylic polymer and natural resin by dissolving the copper salt in water with agitation, by dissolving acrylic polymer in water with agitation, and by dissolving natural resin in water with agitation to form a solution of a fungicidal composition; and
- applying the fungicidal composition solution to plant tissue with the water carrier to enable the fungicidal composition to penetrate the plant tissue to control fungi that may be residing in the plant.

14. The method of claim 13 wherein said fungicidal composition comprises:
- 4–7% by weight copper salt;
- 1–12% by weight acrylic polymer;
- 2–30% by weight natural resin; and
- 51–93% by weight water.

* * * * *